United States Patent [19]

Mattheis

[11] Patent Number: 4,685,596
[45] Date of Patent: Aug. 11, 1987

[54] FLUID DISPENSER

[75] Inventor: Harley H. Mattheis, Verona, N.J.

[73] Assignee: Risdon Corporation, Naugatuck, Conn.

[21] Appl. No.: 855,165

[22] Filed: Apr. 23, 1986

[51] Int. Cl.⁴ ............................................. B67D 5/42
[52] U.S. Cl. .................................. 222/389; 222/399; 604/143
[58] Field of Search ............... 222/145, 136, 135, 389, 222/386, 394, 409, 129, 399; 604/140, 141, 143; 424/51

[56] References Cited

U.S. PATENT DOCUMENTS 2,818,999  1/1958  Miller ................................... 222/389
4,441,629  4/1984  Mackal ................................. 222/389

FOREIGN PATENT DOCUMENTS 1207677 10/1970 United Kingdom ................ 222/389

Primary Examiner—Joseph J. Rolla
Assistant Examiner—Kenneth Noland
Attorney, Agent, or Firm—St. Onge Steward Johnston & Reens

[57] ABSTRACT

A portable device is provided for dispensing fluid in a controlled manner, and, optionally, for mixing two or more fluid components prior to dispensing the resulting mixture. The device comprises a modified syringe provided with needle valve and associated cannula through which fluid is drawn into the syringe chamber and expelled therefrom in a controlled manner by appropriate movement of the piston. In a particular embodiment propellant gas is released behind the piston which, in sealing slidable engagement with the syringe cylinder, thereby exerts expelling pressure on the fluid in the cylinder chamber. The rate of expulsion of fluid from the chamber is regulated by adjustment of the needle valve. The device is especially adapted for mixing two or more liquid components of a periodontal composition and for controlled dispensing of the resulting composition at the locus to be treated.

15 Claims, 4 Drawing Figures

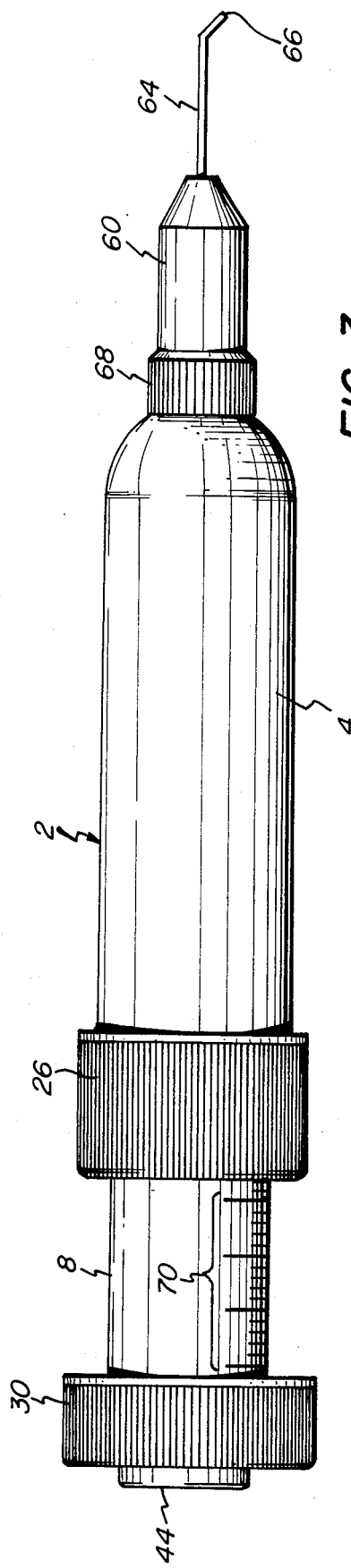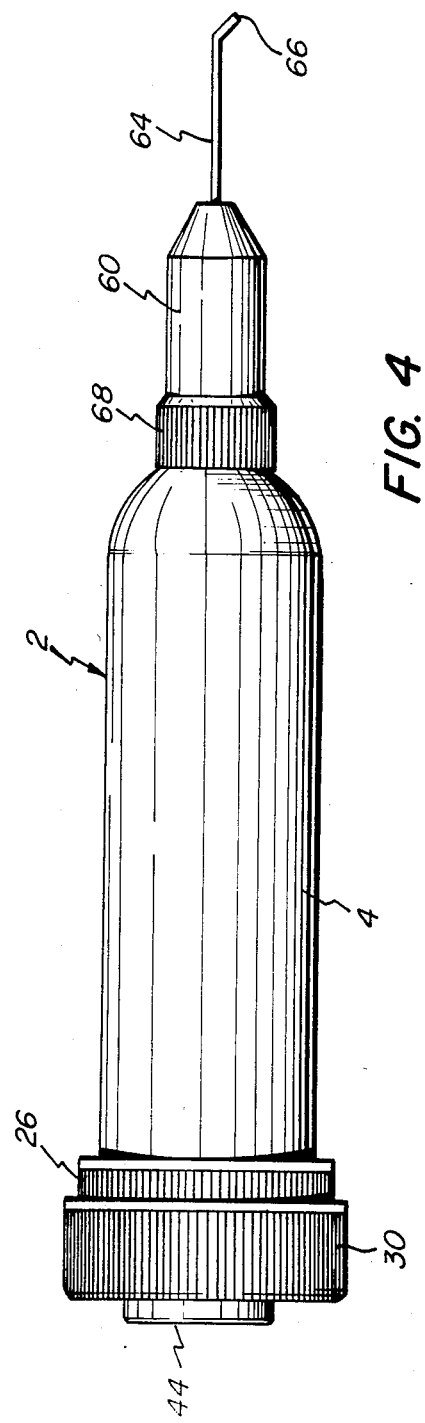

FLUID DISPENSER

BACKGROUND OF THE INVENTION (1) Field of the Invention

This invention relates to the dispensing of fluids and is more particularly concerned with an apparatus and method for mixing two or more fluids and dispensing the mixture in a controlled manner.

(2) Description of the Prior Art

It is desirable to dispense fluid from a relatively inexpensive package which may be disposable after use or which may be recoverable for re-use. In some applications it is desirable to be able to mix fluids from two or more separate containers and then dispense the mixed fluids. This is particularly the case with two or more fluids which may be chemically reactive or unstable when stored in admixture for a prolonged period and which must be dispensed very soon after mixing. A typical situation is that posed by periodontal applications where it is desirable to mix two incompatible chemicals as disclosed in U.S. Pat. No. 4,521,403.

A typical device for dispensing fluids from a plurality of containers is disclosed in McCulloch, U.S. Pat. No. 3,613,956. The latter discloses two aerosol dispensing containers having hollow stems displaceable to discharge fluid under pressure. The actuating mechanism is a handle which pulls the valve stems inward toward their respective containers. The valves are manually pulled inwardly by a trigger which is returned to its original position when it is no longer desired to dispense fluid from the aerosol containers. One of the primary disadvantages of a system that contains aerosol valves that may be repeatedly opened and closed is that the fluid in the containers is not completely dispensed in one actuation of the valves. Since the pressures and the flow rates through the valves may differ from container to container depending upon the type of fluid being dispensed, the size of the valves, and the pressure in the container, the materials may be mixed in undesirable proportions. In addition, if the containers have equal pressures, but the flow rate through the respective valves is different, the head pressure in the mixing chamber may rise to a level where it prevents flow from one of the containers. Thus, the liquids will not be mixed in the desired proportions.

As well as the above disadvantages this type of device suffers the serious problem of bulk which requires the operator to utilize both hands in the dispensing mode. Thus, one hand has to be utilized to actuate and maintain liquid flow and the other hand is utilized to direct the liquid being dispensed to the locus to be treated.

It is accordingly highly desirable to provide a device which will not only mix and dispense fluids but which is of such size and mode of operation as to be held in one hand by an operator and to continue to dispense fluid to the locus to be treated at a controlled rate after actuation without further manual manipulation of the actuating mechanism.

SUMMARY OF THE INVENTION

It is an object of the invention to provide a device for dispensing fluid in a controlled manner without the continuous application of manual pressure by the operator to maintain fluid flow.

It is a further object of the invention to provide a device for dispensing fluid in a controlled manner, which device can be held in one hand by the operator while the fluid being dispensed is directed to a desired location.

It is yet another object of the invention to provide a device which can be utilized to mix two or more fluids and dispense the resulting mixture in a controlled manner without continuous application of manual pressure by the operator to maintain fluid flow.

These objects, and other objects which will become apparent from the description which follows, are achieved by the apparatus and process of the present invention.

In accordance with one aspect of the present invention a fluid dispensing device is provided comprising a piston slidably mounted in a cylinder and defining therewith a chamber for receiving fluid to be dispensed. Valve means, preferably needle valve means, is provided for controlling passage of fluid into and out of said chamber at a controlled rate. Passage of fluid into the chamber is achieved by withdrawing the piston and drawing fluid into the chamber from a source of fluid advantageously through a cannula or like tube associated with the valve means. Dispensing of fluid from the chamber is achieved by providing means for releasing propellant gas under pressure to bias said piston into said chamber. Manual means is provided for actuating release of the propellant gas. This means requires manual operation to commence release of the gas but does not require constant manual pressure throughout the fluid dispensing operation.

In accordance with a preferred aspect of the invention the piston of the device is hollow and has a plunger detachably mounted therein. A container having valve means for dispensing propellant gas under pressure is slidably mounted within the plunger. The valve means on the container is normally biased to a closed position. The container is mounted in the plunger in a manner such that the end portion of the stem of the valve means is received in an appropriately sized and shaped passageway which precludes longitudinal movement of the valve stem relative to the passageway and which terminates in an orifice opening into the interior of the hollow piston. Actuating means is provided for moving the container longitudinally in the plunger which movement causes the valve stem, which is estopped from longitudinal movement in the above passageway, to be depressed and pressurized gas to be released. In order to commence dispensing of fluid from the device, means are provided for detaching the hollow piston from the plunger and means are also provided for locking the plunger in a fixed fluid sealing engagement with the cylinder. When both of these means have been activated the means for release of pressurized gas is actuated. The gas serves to bias the hollow piston into the chamber containing fluid. Controlled dispensing of the fluid is achieved by appropriate manipulation of the valve means on the cylinder.

Where the device is to be used to mix two or more fluids in accurately measured proportions the device is provided with appropriate and visible graduation. The graduation is on the exterior of the cylinder if the latter is sufficiently transparent to reveal the level of liquid contained in the chamber or, alternatively, is on the exterior of the portion of the plunger which is withdrawn from the cylinder as fluid is drawn into the chamber.

Stop means can also be provided for limiting the distance through which the plunger can be withdrawn from the cylinder during the fluid filling operations. Preferably the exterior contour of the portion of the piston received in the cylinder when the plunger is fully inserted therein conforms substantially to the interior contour of the cylinder. The ultimate substantially complete elimination of fluid from the chamber is thereby assured.

BRIEF DESCRIPTION OF THE DRAWINGS

FIG. 3 is a perspective view of the device shown in cross-section in FIG. 1; and, FIG. 4 is a perspective view of the device shown in FIG. 3 with the plunger fully displaced into the cylinder of the device.

DETAILED DESCRIPTION OF THE INVENTION

Figure 1:
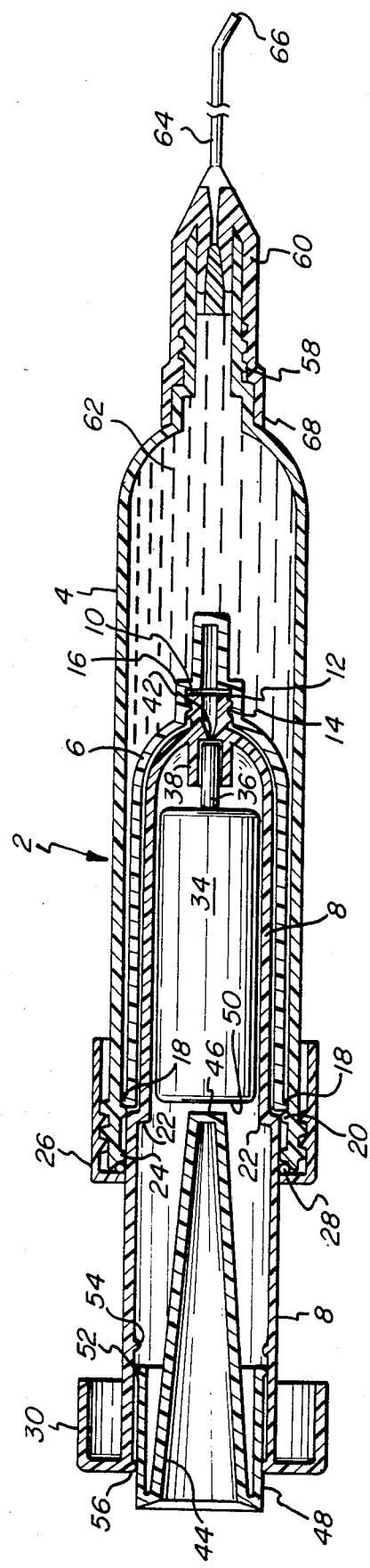
FIG. 1 is a longitudinal cross-sectional view of a device according to the invention showing the plunger in the fully retracted position and fluid drawn in to the chamber thereof.

Referring now to the drawings, FIG. 1 shows a cross-sectional view taken along the longitudinal axis of a fluid dispensing device, shown generally as 2. Cylinder 4 has slidably mounted therein hollow piston 6 which is detachably retained in sleeve-like fashion on the end of plunger 8 by means of interaction of male threads 10 disposed on the exterior of the outer end of passageway 12 and female threads 14 disposed on the interior of throat 16. Annular projection 18 on the outer perimeter of piston 6 engages corresponding annular projection 20 disposed on the inner wall of the upper end of cylinder 4 to prevent accidental withdrawl of piston 6 and attached plunger 8 beyond the position shown in FIG. 1. Step 22 on the wall of plunger 8 receives the rim of the upper end of piston 6 in abutting relationship when the piston is mounted in fixed position on the plunger. The plunger 8 projects outwardly from the upper end of cylinder 4 through the threaded collar 26 and in sliding engagement with the inwardly projecting rim 24 on the upper end of cylinder 4. Collar 26 is threadedly mounted on the end of cylinder 4 and can be tightened by manual rotation in the appropriate direction to lock the plunger 8 in fixed sealing engagement with the cylinder 4 by compression of the O-ring 28 between the abutting surfaces of the underside of collar 26 and the top rim of cylinder 4.

The outer end of plunger 8 projects outwardly from the cylinder 4, in the view shown in FIG. 1, and terminates in skirted flange 30 the underside 32 of which is spaced apart from the outer wall of plunger 8 a distance such that the skirted flange 30 can overlap the collar 26 when the plunger and attached piston 6 are displaced completely into cylinder 4.

Propellant gas container 34 is slidably mounted within plunger 8 with valve stem 36 received in appropriately sized passageway 38 in the throat of said plunger 8. Valve stem 36 is normally biased to the closed position as shown in FIG. 1 but is movable inwardly into the container 34 against the bias to an open position. The tip 40 of valve stem 36 is in abutting, arresting relationship with orifice 42. Displacement of container 34 longitudinally inwardly in said plunger 8 causes the valve stem 36, which is not free to move longitudinally because of interference with orifice 42, to be moved inwardly into the container to the open position.

Actuating knob 44 is mounted in the outer end of plunger 8 with inner end 46 in abutting relationship with bottom 50 of container 34. Knob skirt 48 on knob 44 is in frictional sliding engagement with the inner wall of plunger 8. Annular bead 52 on actuating knob 44 and corresponding annular beads 54 and 56 on the inner wall of plunger 8 serve to define and limit the distance through which knob 44 can be moved longitudinally. The frictional forces exerted by bead 56 on the skirt 48 of knob 44 and bead 52 on the wall of plunger 8 are sufficient to maintain the knob 44 in any desired position against any backward pressure exerted by the container 34 after the latter has been displaced longitudinally by manual pressure exerted on knob 44 in order to actuate valve 36. Alternative means (not shown) of maintaining valve 36 in the open position include the provision of a plurality of interference ribs on the outer wall of container 34 and/or the inner wall of plunger 8 which would maintain the container 34 in its advanced position after being displaced longitudinally by acutation of knob 44.

Neck 58 of cylinder 4 is provided with threaded needle valve 60 (shown in the closed position) which can be rotated axially to open and to provide any desired rate of flow of liquid from chamber 62 for dispensing via the tip 66 of attached cannula 64. The inner contours of neck 58 correspond substantially to the outer contours of throat 16 of piston 6 so that, when piston 6 and attached plunger 8 are fully inserted into cylinder 4, the piston 6 is received in close fitting relationship with the inner end of cylinder 4 and any fluid or air previously present in cylinder 4 is substantially completely displaced therefrom.

The mode of operation of a device according to the invention will now be described with reference to FIGS. 1–4. In order to introduce fluid into chamber 62 the needle valve 60 is opened, piston 6 and attached plunger 8 are thrust fully into cylinder 4 to displace any air therefrom through valve 60 and attached cannula 64. This position is shown in perspective drawing in FIG. 4. Tip 66 of cannula 64 is then immersed in fluid in an appropriate container and a predetermined amount of fluid is drawn into chamber 62 by withdrawing plunger 8 and attached piston 6 an appropriate distance longitudinally in cylinder 4, followed by closure of needle valve 60 advantageously prior to removal of tip 66 from the fluid in the container. The position of piston 6 and attached plunger 8 after drawing fluid into chamber 62 in the above manner is shown in FIGS. 1 and 3.

As shown in FIGS. 3 and 4 the skirted flange 30 is preferably provided with raised ribs or like grip-facilitating means to aid in manual manipulation of plunger 8. Similar grip-facilitating means are preferably also provided on collar 26 of cylinder 4 and on skirt 68 of the needle valve 60.

The amount of fluid drawn into chamber 62 is indicated by scale 70 disposed on the outer wall of plunger 8. Alternatively, when cylinder 4 is fabricated from transparent material which permits the level of fluid in chamber 62 to be observed directly, a corresponding scale can be disposed on the outer wall of cylinder 4 itself.

Where the device 2 is employed to mix two or more different fluids, the required amount of each fluid is drawn into the chamber 62 sequentially in the above manner and the resulting mixture of fluids is thoroughly blended by appropriate shaking of the device 2.

Figure 2:
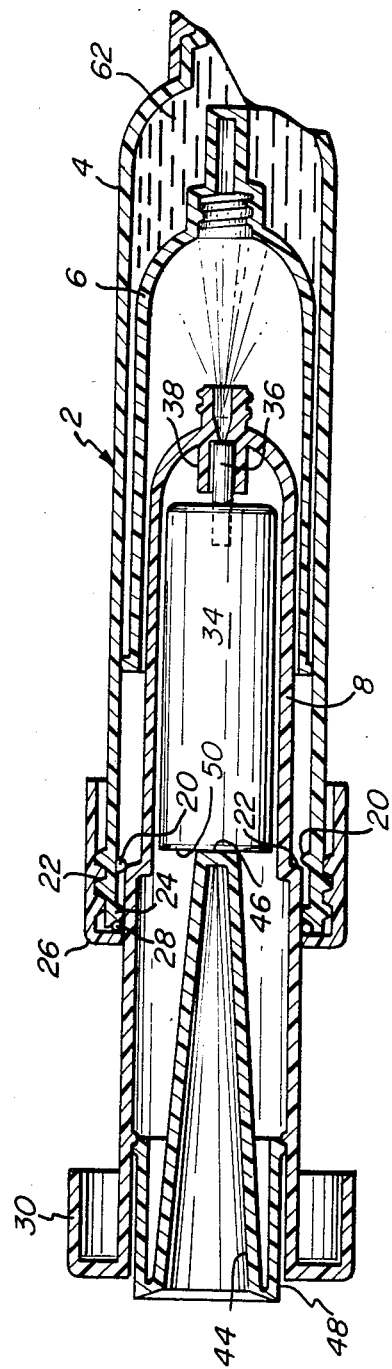
FIG. 2 is a partial longitudinal cross-sectional view of the same device shown in FIG. 1 in the fluid dispensing mode.

The intake of fluid(s) in the above manner leaves the device 2 in the position shown in cross-section in FIG. 1. In order thereafter to convert the device 2 to the liquid dispensing mode, the plunger 8 is first disconnected from piston 6 by appropriate manual rotation of skirted flange 30 to disengage threads 10 and 12. Plunger 8 is then locked firmly in sealing engagement with rim 24 on the upper end of cylinder 4 by screwing threaded collar 26 down tightly so as to compress O-ring 28 between the underside of collar 26 and the upper inwardly sloping surface of rim 24. With plunger 8 locked rigidly in place in this manner, propellant gas container 34 is moved longitudinally in plunger 8 by manual pressure exerted on the outer end of actuating knob 44. Valve stem 36 is thereby caused to move into container 34 thereby relasing pressurized propellant gas from said container via orifice 42 and passageway 12. Detached piston 6 is thereby biased away from plunger 8, as shown in FIG. 2, and pressurizes the fluid in chamber 62. The fluid is then dispensed from the chamber 62 at any desired flow rate by opening and adjusting needle valve 60.

As set forth previously, the frictional forces holding actuating knob 44 in position in plunger 8 are sufficient to retain the knob 44 in the container actuated position so that valve stem 36 remains biased in the open position. Hence it is unnecessary to maintain constant manual pressure on knob 44 in order to maintain flow of liquid from the chamber 62. Thus, once dispensing of liquid has commenced, the dispensing operation can be continued until all fluid has been expelled from chamber 62. Alternatively, if desired, the flow of liquid can be interrupted at any time by closure of needle valve 60 and, optionally, by release of actuating pressure of knob 44 on container 34.

The device 2 is of such size that it can be held conveniently in one hand and, once activated for dispensing in the manner described above, used to deliver fluid to a locus to be treated leaving the other hand of the operator free to carry out whatever additional procedures are necessary concurrently with the liquid dispensing procedure.

The various components which make up the device 2 are preferably fabricated by injection molding or like technique from resilient structural plastic materials such as polypropylene, polycarbonates, polyamides and the like. Because of the resilient nature of such plastics, the piston 6, plunger 8 and actuating knob 44 can be assembled by snapping the former into the cylinder 4 and the latter two into each other in the appropriate order. The cannula 64 is preferably integrally formed on the needle valve 60 as shown in FIGS. 1-4 but can be formed separately and attached to the exit port of needle valve 60 by any appropriate means known in the art.

While the device of the invention can be employed for dispensing of any type of fluid using a hand held instrument it is particularly useful in periodontal applications which normally require the mixing of two or more fluids immediately prior to applying the fluid so formulated to gum tissue. Illustrative of such formulations are those obtained by mixing solutions of providone iodide and hydrogen peroxide in measured proportions.

After use, the device of the invention can be disposed of in any suitable manner. Alternatively, the device can be prepared for re-use by replacing the container of propellant gas with a newly charged container and subjecting the other components of the device to cleaning and sterilization (if necessary).

It is to be understood that, although specific embodiments of the invention have been described herein in detail, such description is for purposes of illustration only and is not intended to be limiting. Modifications which can be made thereto without departing from the scope of the invention will be obvious to those skilled in the art.

What is claimed is:

1. A device for dispensisng fluid comprising:
   a hollow piston slidably mounted in a cylinder and defining therewith a chamber for receiving fluid;
   valve means in said cylinder for receiving fluid into and dispensing fluid from said chamber;
   a plunger having one end detachably mounted in said piston;
   a container having valve means for dispensing propellant fluid, said valve means being normally biased to a closed position, said container being slidably mounted within said plunger;
   means for locking said plunger and said cylinder in fluid sealing engagement;
   detachment means for releasing said piston from said plunger;
   means for actuating said valve means on said container to dispense propellant fluid into said hollow piston after release of the latter from said plunger and thereby bias said piston into said chamber to expel fluid therefrom; and
   means for conducting fluid into, and dispensing fluid from, said chamber.

2. A device according to claim 1 wherein said valve means on said container includes a valve stem movable relative to said container to actuate said valve.

3. A device according to claim 2 wherein the interior of said plunger has a passageway sized and shaped to receive an end portion of said valve stem said passageway terminating in an orifice opening into said hollow piston.

4. A device according to claim 3 wherein said hollow piston and said plunger comprise concentric outer and inner cylindrical members detachably secured together and mounted with said hollow piston in sliding engagement with the inner wall of said cylinder, said container for dispensing propellant fluid being housed in said inner cylindrical member and said orifice traversing the closed end of said inner cylindrical member.

5. A device according to claim 4 and further including means for limiting the distance through which said plunger can be withdrawn from said cylinder.

6. A device according to claim 4 wherein said inner cylindrical member has a longitudinal dimension greater than that of said outer member and approximating that of said cylinder, the outer wall of said inner cylindrical member carrying indicia adapted to be uncovered as said plunger element is withdrawn from said cylinder and representative of the volume of the chamber formed in said cylinder at at least two different stages of withdrawal of said plunger.

7. A device according to claim 6 and further including an actuator projecting into, and slidably mounted in, the open end of said inner cylindrical member and operable by manual pressure to move said container for propellant fluid longitudinally relative to said valve stem in said valve means of said container thereby actuating said valve means.

8. A device according to claim 1 and further including a cannula for conducting fluid into, and dispensing fluid from, said chamber via said valve means.

9. A device according to claim 8 wherein said valve means is a needle valve operable by rotation about its longitudinal axis between a valve open position and a valve closed position.

10. A hand held device for mixing and dispensing fluid comprising:
- a hollow piston slidably mounted in a cylinder and defining therewith a chamber for receiving fluid;
- valve means in said cylinder for controlling flow of fluid into and out of said chamber;
- a plunger having said hollow piston detachably mounted on one end thereof;
- indicia means disposed on said plunger and indicating the volume of said chamber at any given location of said plunger relative to said cylinder;
- means for locking said plunger and said cylinder in fluid sealing engagement;
- detachment means for releasing said piston from said plunger;
- means for releasing propellant gas to bias said piston towards said chamber after release of said piston from said plunger;
- means for actuating said propellant gas releasing means; and
- means for conducting fluid into, and dispensing fluid from, said chamber.

11. A device according to claim 10 wherein said means for releasing propellant as comprises a container for propellant gas mounted slidably in said plunger and having valve means normally biased in closed position said valve means including a valve stem movable relative to said container to open said valve.

12. A device according to claim 11 wherein the end portion of said valve stem is received into a passageway in said plunger said passageway being sized and shaped to receive said valve stem in sealing engagement and prohibiting longitudinal movement of said stem therein when said container is biased towards said passageway.

13. A device according to claim 12 wherein said passageway terminates in an orifice opening into the interior of said piston.

14. A device according to claim 10 and further including a cannula for conducting fluid into, and dispensing fluid from, said chamber via said valve means.

15. A device according to claim 14 wherein said valve means is a needle valve operable by rotation about its longitudinal axis between a valve open portion and a valve closed position.

* * * * *